(12) United States Patent
Margaria

(10) Patent No.: US 7,108,734 B2
(45) Date of Patent: Sep. 19, 2006

(54) SILICON POWDER FOR PREPARING ALKYL- OR ARYL-HALOGENOSILANES

(75) Inventor: Thomas Margaria, Passy (FR)

(73) Assignee: Rhodia Silicones SAS, Lyons (FR)

( * ) Notice: Subject to any disclaimer, the term of this patent is extended or adjusted under 35 U.S.C. 154(b) by 100 days.

(21) Appl. No.: 10/296,548

(22) PCT Filed: May 29, 2001

(86) PCT No.: PCT/FR01/01647

§ 371 (c)(1),
(2), (4) Date: May 9, 2003

(87) PCT Pub. No.: WO01/92153

PCT Pub. Date: Dec. 6, 2001

(65) Prior Publication Data

US 2003/0171606 A1    Sep. 11, 2003

(30) Foreign Application Priority Data

May 30, 2000 (FR) .................... 00 06920

(51) Int. Cl.
- B22F 1/00 (2006.01)
- B22F 9/04 (2006.01)
- C01B 33/08 (2006.01)
- C07F 7/16 (2006.01)

(52) U.S. Cl. ............ 75/255; 75/352; 75/354; 423/342; 241/24.1; 556/472; 556/477

(58) Field of Classification Search ........... 75/255, 75/352, 354; 423/342; 241/24.1; 451/28; 556/472, 477

See application file for complete search history.

(56) References Cited

U.S. PATENT DOCUMENTS

| | | | |
|---|---|---|---|
| 2,466,412 A * | 4/1949 | Gilliam et al. | 556/472 |
| 5,346,141 A | 9/1994 | Kim et al. | |
| 5,728,858 A | 3/1998 | Lewis et al. | |
| 5,783,721 A * | 7/1998 | Tsumura et al. | 556/472 |
| 5,986,123 A * | 11/1999 | Nakayama et al. | 556/472 |
| 6,019,667 A * | 2/2000 | Bush et al. | 451/36 |
| 6,057,469 A | 5/2000 | Margaria et al. | |
| 6,258,970 B1 * | 7/2001 | Ward, III et al. | 556/472 |

FOREIGN PATENT DOCUMENTS

| EP | 0191502 A2 | 8/1986 |
|---|---|---|
| EP | 0893408 A1 | 1/1999 |
| JP | 58145611 | 8/1983 |
| JP | 09141204 | 6/1997 |

* cited by examiner

Primary Examiner—Ngoclan T. Mai
(74) Attorney, Agent, or Firm—Connolly, Bove, Lodge & Hutz, LLP

(57) ABSTRACT

The invention concerns a silicon powder for making alkyl- or aryl-halogenosilanes, with particle-size distribution less than 350 μm, and containing less than 3% and preferably less than 2% of particles having a size less than 5 μm. Said powder enables to improve efficiency of synthesis reaction.

17 Claims, No Drawings

SILICON POWDER FOR PREPARING ALKYL- OR ARYL-HALOGENOSILANES

FIELD OF THE INVENTION

The invention relates to a silicon or silicon alloy powder, of a particle size less than 350 µm, specially adapted for the manufacture of alkyl- or aryl-halogenosilanes, intended for silicone synthesis.

STATE OF THE RELATED ART

The synthesis of alkyl- or aryl-halogenosilanes by means of a reaction between 250 and 350° C. of a halogenated hydrocarbon, for example methyl chloride, on silicon has been known since the patent U.S. Pat. No. 2,380,995 granted in 1945 to E. G. ROCHOW.

This reaction has achieved significant industrial development for silicone manufacture; it is frequently conducted in a fluidised bed reaction vessel with silicon in powder form, most frequently in particle sizes less than 350 µm. For many years, it has been usual to use a fraction with a particle size between approximately 50 and 350 µm, the presence of silicon particles less than 50 µm in size being a cause of material loss and decrease in reaction vessel yield. An illustration of the use of such a particle size distribution can be seen for example in the patent EP 0191502 held by Union Carbide, filed in 1986, which recommends a distribution between 48 mesh (300 µm) and 325 mesh (45 µm), or the application EP 0893408 by Pechiney Electrométallurgie, filed in 1998, which specifies, in examples 1 and 2, a 50–350 µm distribution.

PURPOSE OF THE INVENTION

The invention relates to a silicon or silicon alloy powder for preparing alkyl- or aryl-halogenosilanes, of a particle size of less than 350 µm, comprising a fraction of particles having a size less than 5 µm of less than 3%, and preferentially less than 2%, by weight.

DESCRIPTION OF THE INVENTION

The invention is based on the observation by the applicant of the presence in silicon powders screened to obtain a particle size distribution of around 50 to 350 µm, of non-negligible quantities of particles having a size less than 5 µm. Unexpectedly, experience shows that screening a powder to extract the fraction less than 50 µm proves to be ineffective in eliminating the finest particles, for example the fraction less than 5 µm. These very fine particles are probably generated during the packing of the product and the observation of the powder under a microscope confirms their existence.

The evaluation of their relative quantity by weight can be determined by means of laser granulometry; in silicon powders, irrespective of their preparation method, fractions of particles having a size of less than 5 µm of around at least 4% by weight are always found. The applicant also observed that eliminating or reducing the content of these very fine particles made it possible to improve the Rochow reaction yield. Therefore, the invention consists, in order to use the silicon powder-based contact mass, which represents a significant proportion of the production cost of halogenosilanes, as efficiently as possibly, of reducing the content of particles having a size less than 5 µm to less than 3%, and preferably less than 2%.

To obtain this result, it is possible to use washing with water of the powder ground to less than 350 µm, and screened if required to obtain a particle size distribution of 50–350 µm. This washing is followed by selective decantation, and then drying of the decanted powder and also a vacuum draw-off to facilitate the removal of the water. This technique makes it possible to obtain a strict particle size distribution at 5 µm, the final proportion of the residual fraction having a size less than 5 µm possibly reaching 0.5%.

It is also possible to use, for the selective elimination of the finest particles, dispersion of the powder in a gas stream at a moderate velocity. The velocity of the gas is chosen as a function of the desired cut-off threshold, always operating in the laminar flow state. For the gas, it is preferable to choose oxygen-depleted air for safety reasons.

EXAMPLES

Example 1

A chemical grade metallurgical silicon meeting the required specifications for halogenosilane application was prepared in an electric arc furnace. The alloy was cast, solidified, and then ground to a particle size of less than 350 µm. Five samples of one kg of product were taken.

This type of powder is generally tested on a unit devised to evaluate its performances. In order to do this, 40 g of the powder is mixed with a catalyst and the mixture is placed in a glass reaction vessel 30 mm in diameter equipped with a stirrer. A stream of gaseous $CH_3Cl$ is sent via a sintered glass disk supporting the powder. The gas flow rate is kept constant at $3.6 \cdot 10^{-3}$ m$^3$/hr. After heating the reaction medium and starting the reaction, the system is maintained at 300° C. After 12 hours of reaction, the mean flow rate obtained in dimethyldichlorosilane is noted, along with the content of this product in all the reaction products.

For the evaluation of the particle size grade of the powder of sample No. 1, two types of measurements were made:
- laser granulometry;
- a simplified test with reference to the test described above by working on the test powder directly without adding catalyst, at ambient temperature, with no heating, and by replacing the $CH_3Cl$ gas by nitrogen.

The laser granulometry detected 5.5% (by weight) of fines having a size less than 5 µm.

In the simplified test, after 12 hours of treatment, the product remaining in the reaction vessel was retrieved and weighed. Of the 40 g of the initial product, only 37.2 g remained, i.e. a loss of 7%.

Example 2

Sample No. 2 prepared at the start of example 1 was screened at 50 µm to extract the fraction with a particle size distribution of 0–50 µm. On the sample screened in this way, a laser granulometry measurement was made and detected 4.5% of fines having a size less than 5 µm. 40 g of powder was removed to carry out the simplified test described in example 1. After 12 hours of treatment, the product remaining in the reaction vessel was retrieved and weighed. Of the 40 g of the initial product, only 37.8 g remained, i.e. a loss of 5.5%.

Example 3

Sample No. 3, with a particle size distribution of less than 350 µm, prepared at the start of example 1, was washed in 10 litres of water. The mixture obtained was then allowed to decant for one hour and the supernatant liquor was then eliminated and the decanted powder retrieved and dried under an infrared lamp in a vacuum. On the powder washed in this way, a laser granulometry measurement was made and detected 0.5% fines having a size less than 5 μm.

On said washed sample No. 3, 40 g of powder was removed to carry out the simplified test described in example 1. After 12 hours of treatment, the product remaining in the reaction vessel was retrieved and weighed. Of the 40 g of the initial product, only 39.7 g remained, i.e. a loss of 0.75%.

Example 4

Sample No. 4 prepared at the start of example 1 was dispersed in regular throws at a rate of 10 g per minute at the top of a tube 50 mm in diameter and 500 mm high, with an upward gas stream composed of one volume of air and two volumes of nitrogen running through it, wherein the flow rate was set to 60 cm$^3$ per second.

The removal of a fine dust entrained with the gas was observed at the top of the tube. On the powder retrieved at the base of the tube, a laser granulometry measurement was made and detected 2% fines having a size less than 5 μm.

On said sample No. 4, 40 g of powder was removed to carry out the simplified test described in example 1. After 12 hours of treatment, the product remaining in the reaction vessel was retrieved and weighed. Of the 40 g of the initial product, 39.0 g remained, i.e. a loss of 2.5%.

Example 5

Sample No. 5 was screened at 50 μm to prepare a powder with a particle size distribution of 50–350 μm, which was then used to repeat the operation described in example 4.

On the powder retrieved at the base of the tube, a laser granulometry measurement was made and detected 1% fines having a size less than 5 μm. On said sample No. 5 treated in this way, 40 g of powder was removed to carry out the simplified test described in example 1. After 12 hours of treatment, the product remaining in the reaction vessel was retrieved and weighed. Of the 40 g of the initial product, 39.4 g remained, i.e. a loss of 1.5%.

The invention claimed is:

1. Silicon or silicon alloy powder suitable for preparing alkyl-or aryl-halogenosilanes of a particle size of less than 350 μm, wherein the amount of particles therein having a size less than 5 μm is from 0.5 to 3% by weight, and at least 97% of particles therein have a size from 50–350 μm.

2. Silicon powder according to claim 1, wherein the amount of particles having a size less than 5 μm is less than 2% by weight.

3. A method for preparing the powder according to claim 1, comprising grinding powder to a particle size less than 350 μm, washing with water, decantation and drying.

4. A method according to claim 3, wherein powder ground to less than 350 μm is screened to 50 μm to obtain a particle size distribution of 50–350 μm.

5. A method for preparing the powder according to claim 1, comprising grinding powder to a particle size of less than 350 μm, screening to obtain a particle size distribution of 50–350 μm and dispersion of said powder in a gas stream in the laminar flow state.

6. A method according to claim 5, wherein the gas comprises oxygen-depleted air.

7. A method for preparing alkyl- or aryl-halogenosilanes comprising reacting a halogenated hydrocarbon with a silicon or silicon alloy powder of claim 1, at a temperature from 250°–350° C.

8. A method according to claim 7, wherein the fraction of particles having a size less than 5 μm is less than 2% by weight.

9. A method according to claim 7, wherein the silicon or silicon alloy powder is obtained by grinding powder to a particle size less than 350 μm, washing with water, decontation and drying.

10. A method according to claim 9, wherein the powder ground to less than 350 μm is screened to 50 μm to obtain a particle size distribution of 50–350 μm.

11. A method according to claim 7, wherein the silicon or silicon alloy powder is obtained by grinding of powder to a particle size of less than 350 μm, screening to obtain a particle size distribution of 50–350 μm and dispersion of said powder in a gas stream in the laminar flow state.

12. A method according to claim 11, wherein the gas comprises oxygen-depleted air.

13. A method for preparing the powder according to claim 2, comprising grinding of powder to a particle size less than 350 μm, washing wit water, decantation and drying.

14. A method for preparing powder according to claim 2, comprising grinding powder to a particle size of less than 350 μm, screening to obtain a particle size distribution of 50–350 m and dispersion of said powder in a gas stream in the laminar flow state.

15. A method according to claim 8, wherein the silicon or silicon alloy powder is obtained by grinding powder to a particle size less than 350 μm, washing with water, decantation and drying.

16. A method according to claim 8, wherein the silicon or silicon alloy powder is obtained by grinding powder to a particle size of less than 350 μm, screening to obtain a particle size distribution of 50–350 μm and dispersion of said powder in a gas stream in the laminar flow state.

17. Powder according to claim 1, wherein at least 98% thereof has particle size from 50–350 μm.

* * * * *